United States Patent
Zhang et al.

(10) Patent No.: US 11,786,172 B2
(45) Date of Patent: Oct. 17, 2023

(54) METHOD, DEVICE AND STORAGE MEDIUM FOR SLEEP MONITORING

(71) Applicant: BOE Technology Group Co., Ltd., Beijing (CN)

(72) Inventors: Feng Zhang, Beijing (CN); Yi Li, Beijing (CN); Yao Chen, Beijing (CN); Yajuan Wang, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 396 days.

(21) Appl. No.: 16/990,231

(22) Filed: Aug. 11, 2020

(65) Prior Publication Data

US 2021/0106275 A1 Apr. 15, 2021

(30) Foreign Application Priority Data

Oct. 11, 2019 (CN) .......................... 201910963349.8

(51) Int. Cl.
*A61B 5/00* (2006.01)
*A61B 5/087* (2006.01)
(Continued)

(52) U.S. Cl.
CPC .......... *A61B 5/4815* (2013.01); *A61B 5/0245* (2013.01); *A61B 5/087* (2013.01);
(Continued)

(58) Field of Classification Search
CPC ......... A61B 5/0245; A61B 5/08; A61B 5/087; A61B 5/1135; A61B 5/14542;
(Continued)

(56) References Cited

U.S. PATENT DOCUMENTS 7,041,049 B1 * 5/2006 Raniere ................. A61M 21/02
600/26
10,953,192 B2 * 3/2021 Levendowski ...... A61B 5/4818
(Continued)

FOREIGN PATENT DOCUMENTS

CN 205697716 U 11/2016
CN 107348961 A 11/2017
(Continued)

OTHER PUBLICATIONS

Oswold, C. (2019, May 7). Data Structures: Your quick intro to circular buffers. Medium. Retrieved Sep. 13, 2022, from https://betterprogramming.pub/now-buffering-7a7d384faab5 (Year: 2019).*

(Continued)

*Primary Examiner* — Thaddeus B Cox
*Assistant Examiner* — Marc D. Honrath
(74) *Attorney, Agent, or Firm* — Westman, Champlin & Koehler, P.A.

(57) ABSTRACT

The present disclosure discloses a method, device, apparatus, and storage medium for sleep monitoring. The method includes: monitoring physical sign information of a user in response to receiving a monitoring command; determining sleep quality information of the user according to the physical sign information of the user, wherein the physical sign information comprises at least breathing information.

16 Claims, 6 Drawing Sheets monitoring physical sign information of a user when receiving a monitoring command — S101 determining the sleep quality information of the user according to the physical sign information of the user — S102

(51) Int. Cl.
   *A61B 5/113*     (2006.01)
   *A61B 5/145*     (2006.01)
   *A61M 21/02*     (2006.01)
   *A61B 5/0245*    (2006.01)
   *A61B 5/369*     (2021.01)
   *A61M 21/00*     (2006.01)

(52) U.S. Cl.
   CPC ........ *A61B 5/1135* (2013.01); *A61B 5/14542* (2013.01); *A61B 5/369* (2021.01); *A61B 5/4809* (2013.01); *A61B 5/4818* (2013.01); *A61M 21/02* (2013.01); *A61M 2021/0027* (2013.01); *A61M 2021/0044* (2013.01); *A61M 2021/0083* (2013.01)

(58) Field of Classification Search
   CPC ....... A61B 5/346; A61B 5/369; A61B 5/4809; A61B 5/4815; A61B 5/4818; A61M 2021/0027; A61M 2021/0044; A61M 2021/0083; A61M 2021/0088; A61M 21/00; A61M 21/02; A61M 2205/3317; A61M 2205/3331; A61M 2205/3334; A61M 2205/3553; A61M 2205/3592; A61M 2205/52; A61M 2210/0618; A61M 2210/0625; A61M 2230/04; A61M 2230/10; A61M 2230/205; A61M 2230/40; A61M 2230/63
   See application file for complete search history.

(56) References Cited

U.S. PATENT DOCUMENTS

| 2016/0015315 | A1  | 1/2016  | Auphan et al. |              |
|---|---|---|---|---|
| 2016/0151603 | A1* | 6/2016  | Shouldice     | A61B 5/4806 600/26 |
| 2017/0181635 | A1* | 6/2017  | Liu           | A61B 5/7455  |
| 2018/0116588 | A1* | 5/2018  | Wang          | A61B 5/113   |
| 2019/0007256 | A1* | 1/2019  | Chen          | H04L 27/362  |
| 2019/0175026 | A1* | 6/2019  | Verzal        | G06F 21/6245 |
| 2019/0246952 | A1* | 8/2019  | Groenendaal   | A61B 5/0826  |
| 2020/0375528 | A1* | 12/2020 | Flanagan      | A61B 5/087   |

FOREIGN PATENT DOCUMENTS

| CN | 108245762 A   |   | 7/2018 |
|---|---|---|---|
| CN | 108309286 A   |   | 7/2018 |
| KR | 102119805 B1  | * | 2/2019 |
| WO | 2018099114 A1 |   | 6/2018 |

OTHER PUBLICATIONS

Nalevka, P. (Oct. 24, 2010). Sleep as Android: Smart Alarm User Manual. Sleep as Android: Smart Alarm. Retrieved Sep. 13, 2022, from https://docs.sleep.urbandroid.org/ (Year: 2010).*

Hang, L.-W., Wang, H.-L., Chen, J.-H., Hsu, J.-C., Lin, H.-H., Chung, W.-S., & Chen, Y.-F. (2015). Validation of overnight oximetry to diagnose patients with moderate to severe obstructive sleep apnea. BMC Pulmonary Medicine, 15(1). https://doi.org/10.1186/s12890-015-0017-z (Year: 2015).*

Oswold, C. (May 7, 2019). Data Structures: Your quick intro to circular buffers. Medium. Retrieved Sep. 13, 2022, from https://betterprogramming.pub/now-buffering-7a7d384faab5 (Year: 2019).*

Obstructive sleep apnea. Thoracic Key. (Jul. 21, 2019). Retrieved Mar. 13, 2023, from https://thoracickey.com/obstructive-sleep-apnea/ (Year: 2019).*

Copy of first Office Action, including Search Report, for Chinese Patent Application No. 201910963349.8, dated Oct. 12, 2022, 19 pages.

* cited by examiner

# METHOD, DEVICE AND STORAGE MEDIUM FOR SLEEP MONITORING

CROSS-REFERENCE TO RELATED APPLICATION(S)

This application claims priority to Chinese Patent Application No. 201910963349.8, entitled "Method, Device, Apparatus and Storage Medium for Sleep Monitoring" and filed on Oct. 11, 2019, which is incorporated herein by reference in its entirety.

TECHNICAL FIELD

The present disclosure relates to the field of health and medical technology, and in particular, to a method, device, and storage medium for sleep monitoring.

BACKGROUND

Sleep occupies an important position in people's daily life and has a great impact on people's quality of life. For people with sleep disorders, the type and severity of sleep disorders may be known through sleep monitoring, and then different intervention schemes may be taken. Polysomnography (PSG) is the current standard for diagnosing sleep apnea-hypopnea syndrome, but it is expensive, complicated to use, and difficult to achieve widespread popularity and application. Other common sleep monitoring products on the market usually only evaluate the sleep status based on a single breathing indicator, and cannot accurately evaluate the sleep states of users, and users cannot know in time their possible sleep disorders.

SUMMARY

The purpose of the embodiments of the present disclosure is to provide a sleep monitoring method, device, and storage medium, so as to solve the problem in the related art that the sleep states of users cannot be accurately evaluated, and users cannot know in time their possible sleep disorders.

In order to solve or at least alleviate the above technical problems, the embodiments of the application adopt the following technical solution. A method for sleep monitoring comprises: monitoring a physical sign information of a user when receiving a monitoring command; determining sleep quality information of the user according to the physical sign information of the user, wherein the physical sign information comprises at least breathing information.

In some embodiments, the breathing information is determined according to at least one of: oronasal airflow information, thoracoabdominal motion information, and pressure sensing information.

In some embodiments, the physical sign information further comprises at least one of: blood oxygen information, electroencephalogram information, body movement information, and electrocardiogram information.

In some embodiments, the thoracoabdominal motion information is obtained by using a biological radar wave.

In some embodiments, the sleep quality information comprises at least one of: a number of sleep apnea, durations of sleep apnea, and blood oxygen drop data.

In some embodiments, the determining the sleep quality information of the user according to the physical sign information of the user comprises: in a case where the breathing information is determined according to the oronasal airflow information, determining the number and/or the durations of the sleep apnea according to the oronasal airflow information or according to the blood oxygen information and the oronasal airflow information.

In some embodiments, the determining the sleep quality information of the user according to the physical sign information of the user comprises: in a case where the breathing information is determined according to the thoracoabdominal motion information, determining the number and/or the durations of the sleep apnea according to the thoracoabdominal motion information or according to the thoracoabdominal motion information and at least one of the body movement information and the electrocardiogram information.

In some embodiments, the determining the sleep quality information of the user according to the physical sign information of the user comprises: in a case where the breathing information is determined according to the thoracoabdominal motion information, determining the blood oxygen drop data according to the blood oxygen information, or determining the blood oxygen drop data according to the blood oxygen information and the thoracoabdominal motion information.

In some embodiments, the sleep quality information further comprises at least one of: falling asleep time, awaking time, light sleep duration, and deep sleep duration.

In some embodiments, the determining the sleep quality information of the user according to the physical sign information of the user comprises: determining the falling asleep time and/or the awaking time according to at least one of: the electroencephalogram information, the electrocardiogram information, and the body movement information.

In some embodiments, the determining the sleep quality information of the user according to the physical sign information of the user comprises: in a case where the breathing information is determined according to the thoracoabdominal motion information and/or the oronasal airflow information, determining the falling asleep time and/or the awaking time according to at least one of: the thoracoabdominal motion information, the oronasal airflow information, the electroencephalogram information, the electrocardiogram information and the body movement information.

In some embodiments, the determining the sleep quality information of the user according to the physical sign information of the user comprises: determining the deep sleep duration and/or light sleep duration of the user according to the electroencephalogram information and/or the body movement information.

In some embodiments, before monitoring the physical sign information of the user when receiving the monitoring command, the method further comprises: detecting whether a sleep assistance command is received; in response to receiving the sleep assistance command, lighting up a breathing light at a preset frequency and/or playing sleep assistance music.

In some embodiments, the method further comprises: detecting whether the user enters into a sleep state according to the physical sign information; when the user enters into the sleep state, gradually reducing a brightness of the breathing light within a first preset duration until the breathing light is extinguished; and/or gradually reducing a playback volume of the sleep assistance music within a second preset duration until the sleep assistance music stops playing.

In some embodiments, the method further comprises: detecting whether current time reaches a first wake-up time; when the current time reaches the first wake-up time, detecting whether the user is in a light sleep state according` to the physical sign information; when the user is in the light sleep state, turning on a wake-up device, and gradually increasing a prompt intensity of the wake-up device to a preset intensity within a third preset duration; when the user is not in the light sleep state, detecting whether the current time reaches a second wake-up time; when the current time reaches the second wake-up time, turning on the wake-up device at the preset intensity; wherein the first wake-up time is earlier than the second wake-up time.

In some embodiments, the method further comprises: when the wake-up device is on, detecting whether a wake-up device stop command is received; if the wake-up device stop command is received, turning off the wake-up device; if the wake-up device stop command is not received, detecting whether a wake-up device pause command is received; if the wake-up device pause command is received, temporarily turning off the wake-up device, and turning on the wake-up device again after a preset pause duration; if the wake-up device pause command is not received, temporarily turning off the wake-up device after the wake-up device is turned on for a fourth preset duration, and turning on the wake-up device again after the preset pause duration; turning off the wake-up device after the wake-up device is paused for a preset number of times.

In some embodiments, after the wake-up device is turned off, the monitoring of the physical sign information of the user is stopped.

In some embodiments, the method further comprises: when a music playback address is received, detecting whether a occupied space of buffered music files exceeds a preset buffer space; when the occupied space exceeds the preset buffer space, deleting a music file with the earliest buffer time among the buffered music files; buffering a music file corresponding to the music playback address and playing the music file.

An embodiment of the present disclosure also discloses a device for sleep monitoring comprising: a communication circuit configured to receive a control command from a user; a physical sign monitoring circuit configured to monitor physical sign information of the user and output the physical sign information to a processor; wherein the physical sign monitoring circuit comprises at least a breathing monitoring circuit configured to monitor breathing information of the user; the processor, communicatively coupled with the communication circuit and the physical sign monitoring circuit and configured to: when the communication circuit receives a monitoring command, receive the physical sign information output by the physical sign monitoring circuit, and determine the sleep quality information of the user based on the physical sign information of the user.

An embodiment of the present disclosure also discloses a non-transitory computer-readable storage medium having stored thereon a computer program that, when executed by a processor, causes the processor to perform the foregoing method.

BRIEF DESCRIPTION OF THE DRAWINGS

In order to more clearly illustrate the technical solutions in the embodiments of the present disclosure or the related art, the attached drawings, which are to be used in the descriptions of the embodiments or the related art, will be briefly described below. It is apparent that the attached drawings in the following descriptions are merely embodiments of the present disclosure, and other drawings may be obtained by those skilled in the art based on these drawings without creative efforts.

DETAILED DESCRIPTION

Some schemes and features of the application are described herein with reference to the drawings.

It should be understood that various modifications may be made to the embodiments applied herein. Therefore, the above description should not be viewed as limiting, but merely as an example of an embodiment. Those skilled in the art will envision other modifications within the scope and spirit of the application.

The accompanying drawings, which are incorporated in and constitute a part of the specification, illustrate embodiments of the application, and together with a general description of the application given above and a detailed description of the embodiments given below, serve to explain principle of the application.

These and other features of the application will become apparent from the following description of some embodiments given as non-limiting examples with reference to the accompanying drawings.

It should also be understood that although the application has been described with reference to some specific examples, those skilled in the art can definitively implement many other equivalent forms of the application, which have the features as set forth in the claims and are therefore all within the scope of protection defined by the claims.

The above and other aspects, features, and advantages of the present application will become more apparent in view of the following detailed description when combined with the accompanying drawings.

Hereinafter, specific embodiments of the application will be described with reference to the drawings; however, it should be understood that the applied embodiments are merely examples of the application, which may be implemented in various ways. Well-known and/or repetitive functions and structures will not be described in detail to avoid unnecessary or redundant details that make the application ambiguous. Therefore, the specific structural and functional details filed herein are not intended to be limiting, but merely serve as a basis and representative basis for the claims to teach those skilled in the art to variously use the application in substantially any appropriate detailed structure.

This specification may use the phrases "in one embodiment", "in another embodiment", "in yet another embodiment" or "in other embodiments", which may all refer to one or more of the same or different embodiments according to the application.

Figure 1:
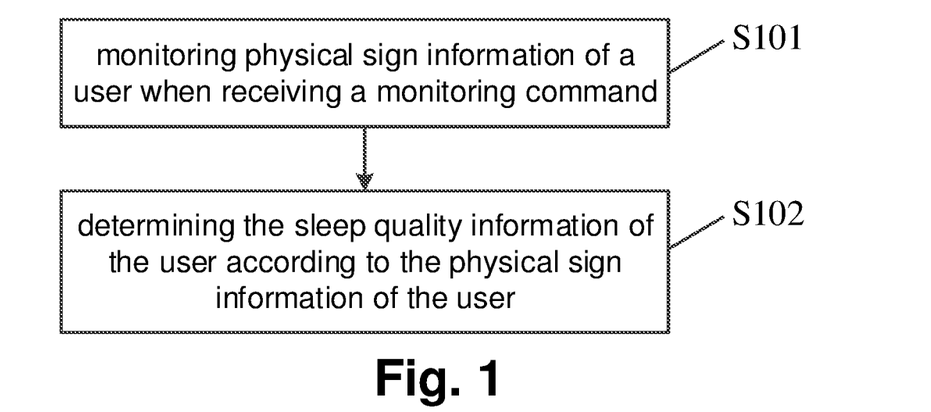
FIG. 1 is a flowchart of a sleep monitoring method according to an embodiment of the present disclosure.

Some embodiments of the present disclosure provide a sleep monitoring method, which is mainly applied to a sleep monitoring apparatus with the function of monitoring a user's physical sign. The flowchart is shown in FIG. 1 and mainly includes steps S101 and S102:

S101, monitoring physical sign information of a user when receiving a monitoring command;

S102, determining the sleep quality information of the user according to the physical sign information of the user.

At present, the common sleep monitoring apparatus are usually placed at a position closer to the user in which the user's physical information can be learned in time. Before preparing to sleep, the user usually puts the sleep monitoring apparatus into a monitoring mode by sending a monitoring command to the sleep monitoring apparatus. The monitoring command may be a physical button or a touch area provided on the body of the sleep monitoring apparatus. The user sends the monitoring command to the processor of the apparatus by pressing, tapping, or touching, or the like. Alternatively, the user sends the monitoring command through a mobile terminal that can send the command to the apparatus.

In actual use, users may also set a time for sleep monitoring in advance, such as actively turning on the monitoring mode for sleep monitoring at 22:00 every night. It should be understood that the commands sent through the physical buttons or the mobile terminal may not be limited to the monitoring commands. The user may send all the control commands mentioned in this embodiment through the physical buttons or the mobile terminal (or more generally, another apparatus).

After receiving the monitoring command or reaching the preset sleep monitoring time, the monitoring apparatus starts to monitor the user's physical signs and obtains the corresponding physical sign information. The monitoring is performed in real time, and the monitoring apparatus will continuously monitor the user while the monitoring mode is on. The user's physical sign information, which mainly includes breathing information and blood oxygen information, is monitored by various monitoring apparatus that are either installed in the sleep monitoring apparatus or capable of performing data communication with the sleep monitoring apparatus. In some embodiments, the user's physical sign information may also include other physical sign information such as electroencephalogram information, body movement information, and electrocardiogram information.

Specifically, the breathing information is information reflecting the breathing situation of the user, and it may be determined through information such as oronasal airflow information, thoracoabdominal motion information, and pressure sensing information. The oronasal airflow information may be obtained by the airflow sensor placed near the user's mouth and nose, the thoracoabdominal motion information may be obtained by biological radar waves, and the pressure sensing information may be obtained by the pressure sensor placed on the user's thoracoabdominal. The purpose is to obtain the user's breathing situation, as a monitored user's physical sign information. In addition, the determination method of the breathing information is not limited to the several methods described in this embodiment. In actual use, the breathing information of the user may also be determined through other methods, which is not limited in this embodiment.

The sleep quality information is information that reflects the user's sleep situation and is the basis for users to understand their own sleep quality. In this embodiment, the sleep quality information mainly includes the number and/or durations of sleep apnea and blood oxygen drop data (i.e. data indicating drop of blood oxygen content), and may also include basic sleep information, such as the falling asleep time, the duration of deep sleep (that is, the deep sleep duration), the duration of light sleep (that is, the light sleep duration), and the wake-up time during this sleep. In some embodiments, the sleep monitoring apparatus may further generate a sleep quality report according to the sleep quality information. The above sleep quality information may be reflected in the sleep quality report in various forms such as tables, fan charts, and line charts. In addition, the sleep quality report may also provide the basis for judging the occurrence of sleep apnea and suggestions for adjustment. When the situation is relatively serious, the sleep quality report may also recommend users to seek medical treatment in a timely manner. The conclusions in the sleep quality report may be generated by the sleep monitoring apparatus, or the physical sign information may be uploaded to a cloud server through the network, combined with big data for more detailed judgment.

When the user's breathing information is determined according to the oronasal airflow information, the number and/or durations of sleep apnea during the sleep process of the user may be determined according to the blood oxygen information and/or the oronasal airflow information. Specifically, sleep apnea is one of the common sleep disorders. Symptoms of snoring, belching and other inability to breathe during sleep at night are common manifestations of sleep apnea. In severe cases, the cardiovascular system is involved, or asphyxia or sudden death occurs. In this embodiment, if the user develops sleep apnea, the generation of airflow will not be monitored at his or her mouth and nose. Further, in the absence of normal breathing, the user will not be supplemented with oxygen and the blood oxygen content will possibly decrease. Therefore, according to the oronasal airflow information alone or according to the blood oxygen information and the oronasal airflow information, it can be determined whether the user has sleep apnea during sleep, and the number of occurrences and/or the accumulated duration of apnea in the case of sleep apnea can be recorded and output to the user as the sleep quality information.

When the user's breathing information is determined according to the thoracoabdominal motion information, the blood oxygenation information and the thoracoabdominal motion information may be combined to determine the blood oxygen drop data of the user during sleep. Specifically, the blood oxygen drop is the decrease in blood oxygen content caused by apnea. When it is severe, it may easily lead to insufficient blood supply to the heart and brain, causing serious harm to the user's body. In this embodiment, whether the user's blood oxygen has reduced is mainly determined according to the user's blood oxygen information. In some embodiments, it may be further combined with the determination, through the thoracoabdominal motion information, of the breathing situation of the user to make a more accurate determination of whether the user's blood oxygen has reduced. When the user's blood oxygen has reduced, the detailed blood oxygen drop data may be recorded so that the user may subsequently know his or her condition or use the recorded data as a basis for diagnosis.

When determining the user's falling asleep time and/or awaking time, it is mainly determined by at least one of electroencephalogram information, electrocardiogram information and body movement information. When the user's brain waves reflected by the electroencephalogram information are no longer excited and calm, or when the heartbeat frequency of the user is reduced according to the electroencephalogram information, or when it is reflected that the user has not experienced body movement for a period of time according to the body movement information, it can be determined that the user has entered the sleep state, otherwise it proves that the user has ended the sleep state. The corresponding time may be recorded as the user's falling asleep time or awaking time. When the thoracoabdominal motion information and/or the oronasal airflow information of the user are also obtained, the user's falling asleep time and awaking time may also be determined based on the above physical sign information in combination with the thoracoabdominal motion information or the oronasal airflow information, in order to achieve a more accurate judgment of the user's falling asleep time and awaking time.

When determining the deep sleep duration and light sleep duration of a user, the determination is mainly based on the electroencephalogram information and/or the body movement information. When using the electroencephalogram information, it is determined whether the user is in deep sleep or light sleep according to the rules reflected by the brain waves, and the duration of deep sleep and light sleep is separately counted as the sleep quality information. When using the body movement information, the determination of deep sleep or light sleep may be based on the user's body movement, but compared with the use of electroencephalogram information, the accuracy of the determination using body movement information is lower. Generally, the body movement information is used as the reference information of the electroencephalogram information. Through the combination of the electroencephalogram information and body movement information, the accuracy of the determination of deep sleep state and light sleep state is improved.

In some embodiments, in addition to monitoring the user's sleep, the embodiment can also assist the user to quickly enter the sleep state by playing sleep assistance music or lighting the breathing light, thereby helping the user to develop good sleep habits and reduce the possibility of occurrence of sleep disorders. Specifically, according to the flowchart shown in FIG. 2, when the user wishes to perform sleep assistance, the user sends a sleep assistance command to the apparatus, and the apparatus enters a sleep assistance mode after receiving the sleep assistance command. In the sleep assistance mode, the apparatus lights up a breathing light at a preset frequency to help the user adjust his or her breathing rhythm, or plays different types of sleep assistance music to help the user relax and then quickly enter the sleep state. The user's good sleep habits may be cultivated through long-term sleep assistance. Sleep assistance music mainly includes white noise (such as water flow, raindrops, waves, and the like), sleep assistance pure music (such as soothing piano music), breathing meditation courses (such as mindfulness meditation music) or other music set by the user. The user may select which music to play for sleep assistance by sending different control commands.

Figure 2:
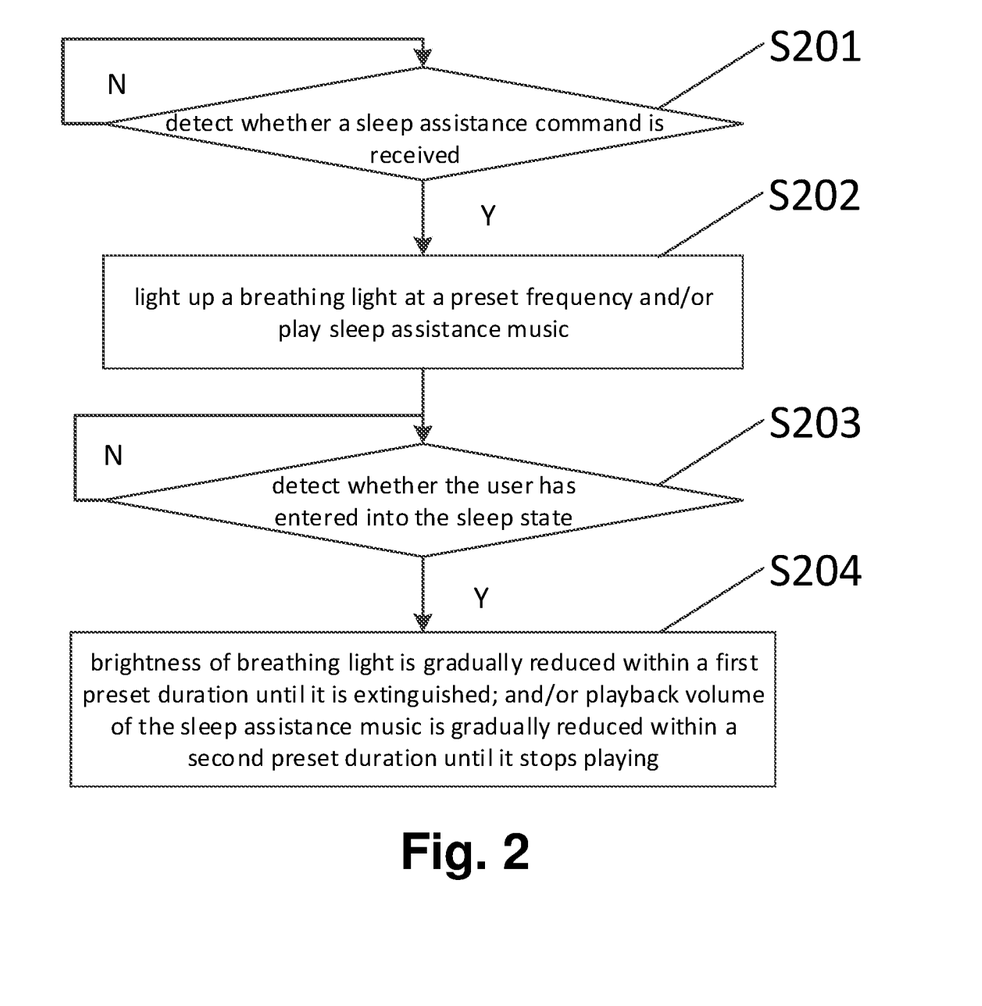
FIG. 2 is a schematic flowchart of implementing a sleep assistance function according to an embodiment of the present disclosure.

While the breathing light is flashing or the music is being played, the sleep monitoring apparatus needs to detect whether the user has entered the sleep state according to the user's physical sign information. After determining that the user has entered the sleep state, if the breathing light still flashes, then the brightness of the breathing light is gradually reduced until the breathing light is extinguished within a first preset duration; or if the sleep assistance music is being played, the playback volume of the sleep assistance music is gradually reduced until the sleep assistance music stops playing within a second preset duration. The first preset duration and the second preset duration may be the same or different, and the specific time is set according to user needs. Since the user is usually in a light sleep state when entering the sleep state, the user is easily awakened if there is a sudden change in brightness or ambient volume. Therefore, the effect of the external environment on the user's sleep is reduced by gradually reducing the brightness and gradually reducing the volume, thus improving the user's sleep quality. In addition, if the user has not entered the sleep state after the sleep assistance music is played or the breathing light flashes for a certain period of time, the breathing light is automatically turned off or the music is automatically stopped, or the apparatus waits for the user to send a sleep assistance command again.

Figure 3:
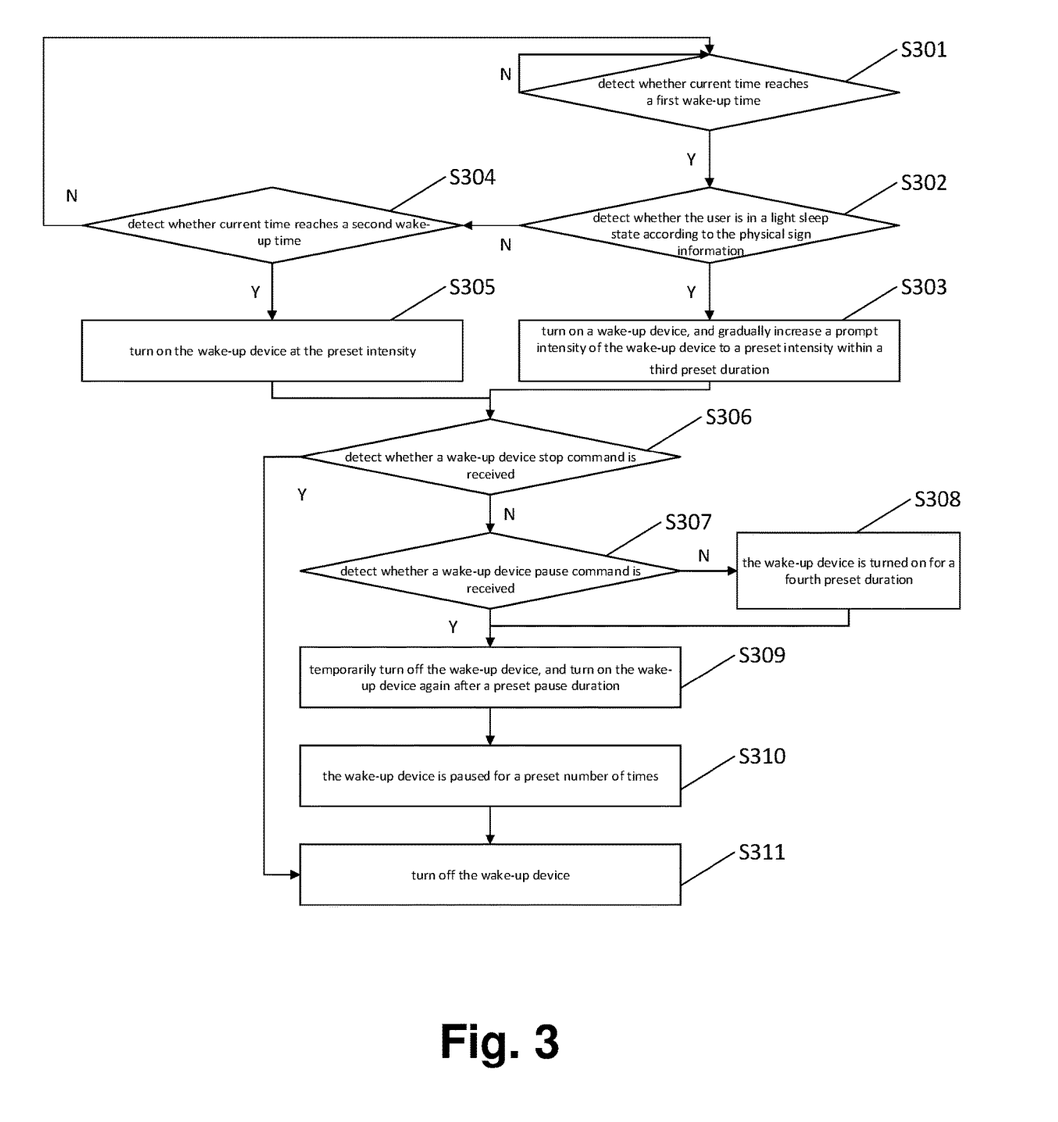
FIG. 3 is a schematic flowchart of implementing a wake-up function according to an embodiment of the present disclosure.

The sleep monitoring apparatus described in this embodiment may also provide a user with a natural wake-up function. Before going to bed, the user usually sets a wake-up apparatus such as an alarm clock and a timer to wake up the user at a predetermined time. In this embodiment, the wake-up time set by the user is a second wake-up time, and a first wake-up time, which is earlier than the second wake-up time, is set as the time to naturally wake up the user. As shown in FIG. 3, when the user is in the sleep state, the sleep monitoring apparatus continuously detects whether the current time reaches the first wake-up time, that is, whether it is the time to naturally wake up the user. If the current time reaches the first wake-up time, it is determined whether the user is in a light sleep state based on the currently acquired physical sign information of the user. During the light sleep, the user's cerebral cortex is in a relatively active stage, and it is easy to wake up the user at this time. Therefore, when the user is in the light sleep state, a wake-up device is turned on, and a prompt intensity of the wake-up device is gradually increased to a preset intensity within a third preset duration, thus the effect of awakening the user is gradually strengthened, which prevents the user from being awakened by a sudden strong prompt and prevents user experience from being affected. If the user is not in the light sleep state at the first wake-up time, it is detected whether the current time reaches the second wake-up time set by the user, that is, the time that the user must be woken up. If the second wake-up time is reached, the wake-up device is directly turned on with the preset intensity to achieve wake-up of the user. If the second wake-up time is not reached, it is re-detected whether the first wake-up time is reached.

Specifically, the prompting method of the wake-up device includes at least a vibration prompt and a sound prompt. When the wake-up device uses the vibration method to wake up the user, the frequency of vibration may be gradually increased within a third preset duration to continuously improve the wake-up effect on the user. When the wake-up device uses the sound prompt to wake up the user, the volume of the sound may be gradually increased within a third preset duration to continuously improve the wake-up effect on the user. The above two prompt methods may be used simultaneously, and other wake-up methods may also be added. As long as the wake-up effect for the user can be achieved, this embodiment is not limited thereto.

By awakening the user naturally in advance, this embodiment can make the user wake up more comfortable, cultivate the user's good working and rest habits, adjust the user's biological clock, and then improve the user's sleep quality and ensure a better mental state during the day. In some embodiments, the first wake-up time is earlier than the second wake-up time, and the time difference between the two may be 10 minutes or may be set by the user. The third preset duration should be less than the time difference between the first wake-up time and the second wake-up time, preferably 60 seconds, and may also be set according to user needs, which is not limited in this embodiment.

When the user needs to turn off the wake-up device, he or she may control its stop by sending different stop commands, as shown in FIG. 3. When the wake-up device is on, it first detects whether a wake-up device stop command from the user is received. This command may be sent by a mobile terminal or generated by the user's tap or press on the key or touch area of the apparatus. For example, a long press of the touch area for three seconds corresponds to the wake-up device stop command. When the wake-up device stop command is received, the wake-up device will be directly turned off. If the wake-up device stop command is not received, it is determined whether a wake-up device pause command is received. The wake-up device pause command may also be sent by a terminal, or generated by touching or pressing the key or touch area of the apparatus, but the way of pressing or touching should be different from that of the wake-up device stop command. For example, it may be generated by touching the touch area once. When the wake-up device pause command is received, the wake-up device is turned off temporarily to enter a nap mode, and is turned on again after a preset pause duration to receive the commands from the user again. If neither the wake-up device stop command nor the wake-up device pause command is received, the wake-up device is turned on for a fourth preset duration and then temporarily turned off, and then turned on again after a preset pause duration. If the wake-up device stop command is never received, the wake-up device will be completely turned off after repeatedly turning on and off for a preset number of times, to prevent the user from being disturbed by the wake-up device being turned on for a long time. Specifically, each of the preset pause duration, the fourth preset duration, and the preset number of times may be set according to user needs, which is not limited in this embodiment.

Figure 4:
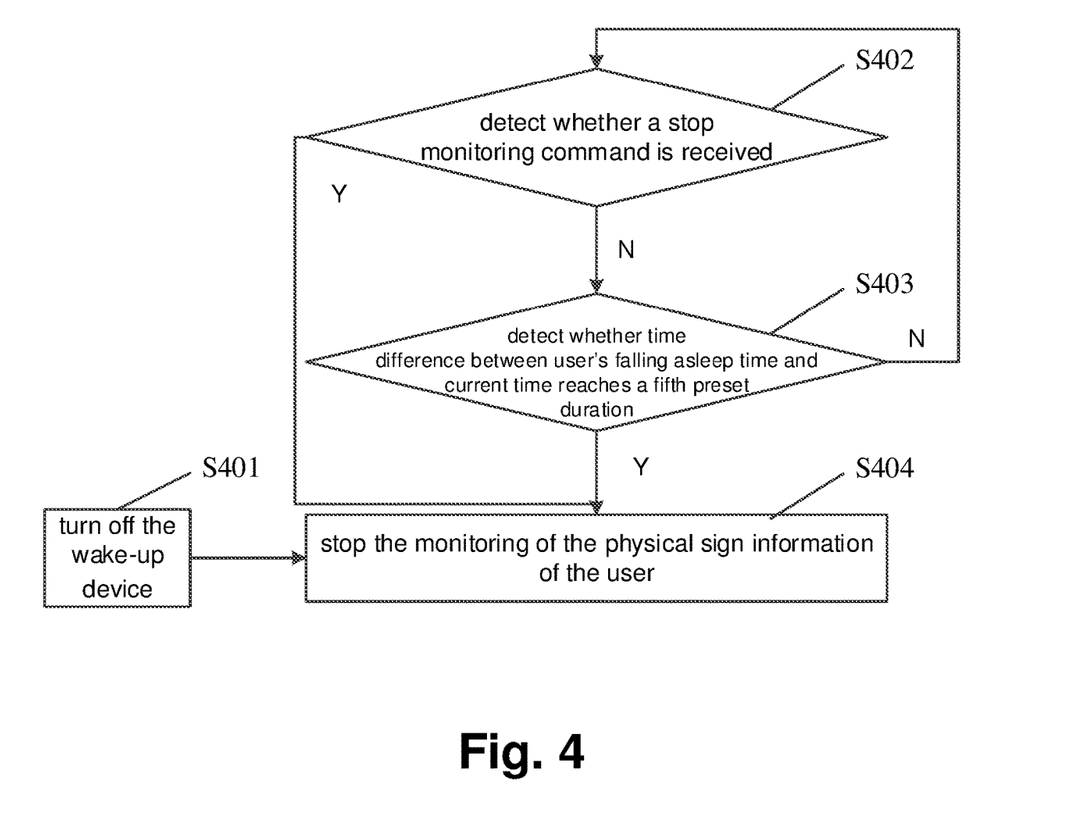
FIG. 4 is a schematic flowchart of stopping the monitoring of physical sign information of a user according to an embodiment of the present disclosure.

FIG. 4 shows a flowchart of stopping the monitoring of the user's physical sign information in this embodiment. As shown in FIG. 4, when the wake-up device is turned off, the sleep monitoring apparatus turns off the monitoring mode and stops monitoring the user's physical sign information. In addition, the monitoring mode may also be turned off according to a stop monitoring command. Specifically, it is detected whether the stop monitoring command sent by the user is received, and the stop monitoring command may be sent by a mobile terminal or generated by the user's tapping or pressing of the key or touch area of the apparatus. For example, a long press of a physical button for 3 seconds corresponds to the stop monitoring command. Upon receiving the stop monitoring command, the monitoring of the user's physical sign information is stopped. If the stop monitoring command is not received, it is detected whether the time difference between the user's falling asleep time and the current time reaches a fifth preset duration. The fifth preset duration may be set to the duration of a normal person's sleep, such as 8 hours. After the time difference exceeds 8 hours, the user's sleep state ends, and the monitoring of the user's physical sign information in the sleep state is automatically stopped. If it is detected that the time difference between the user's falling asleep time and the current time does not reach the fifth preset duration, the monitoring is continued until a stop monitoring command is received or the time difference reaches the fifth preset duration.

Figure 5:
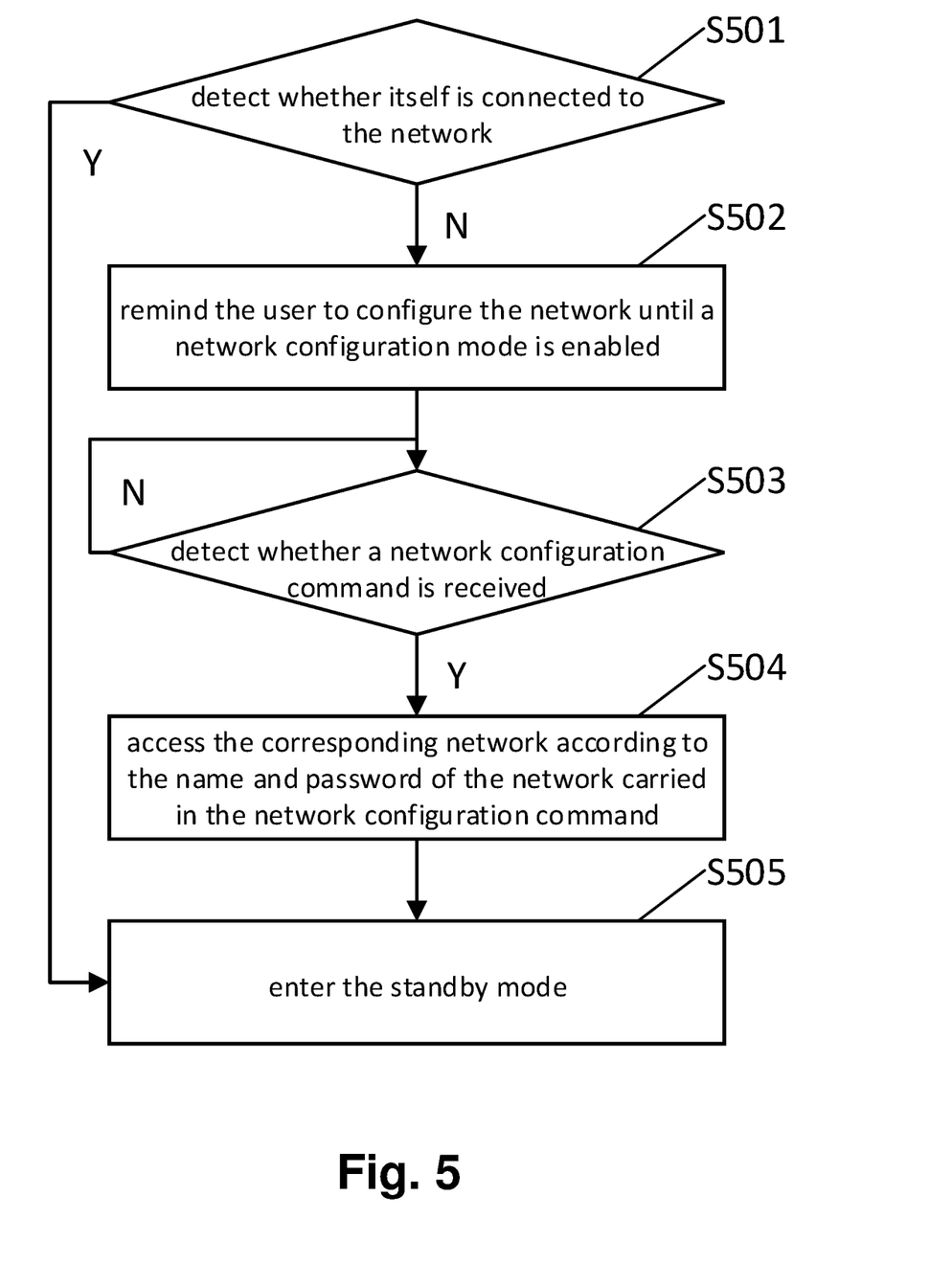
FIG. 5 is a schematic flowchart of the network configuration according to an embodiment of the present disclosure.

FIG. 5 shows a flowchart of network configuration in this embodiment. As shown in FIG. 5, after the sleep monitoring apparatus is powered on, it first detects whether it is connected to the network. When connected to the network, it directly enters the standby mode. When not connected to the network, the apparatus reminds the user to configure the network by flashing an indicator light or issuing an alarm sound. At this time, the user may turn on the apparatus's network configuration mode by long pressing a physical button for 5 seconds. In the network configuration mode, the apparatus continuously detects whether a network configuration command is received. The network configuration command may be sent by the user's mobile terminal, and the command carries the name and password of the network. The apparatus accesses the corresponding network according to the name and password of the network, so as to obtain update services or data support from the network. The apparatus enters standby mode after connecting to the network.

Figure 6:
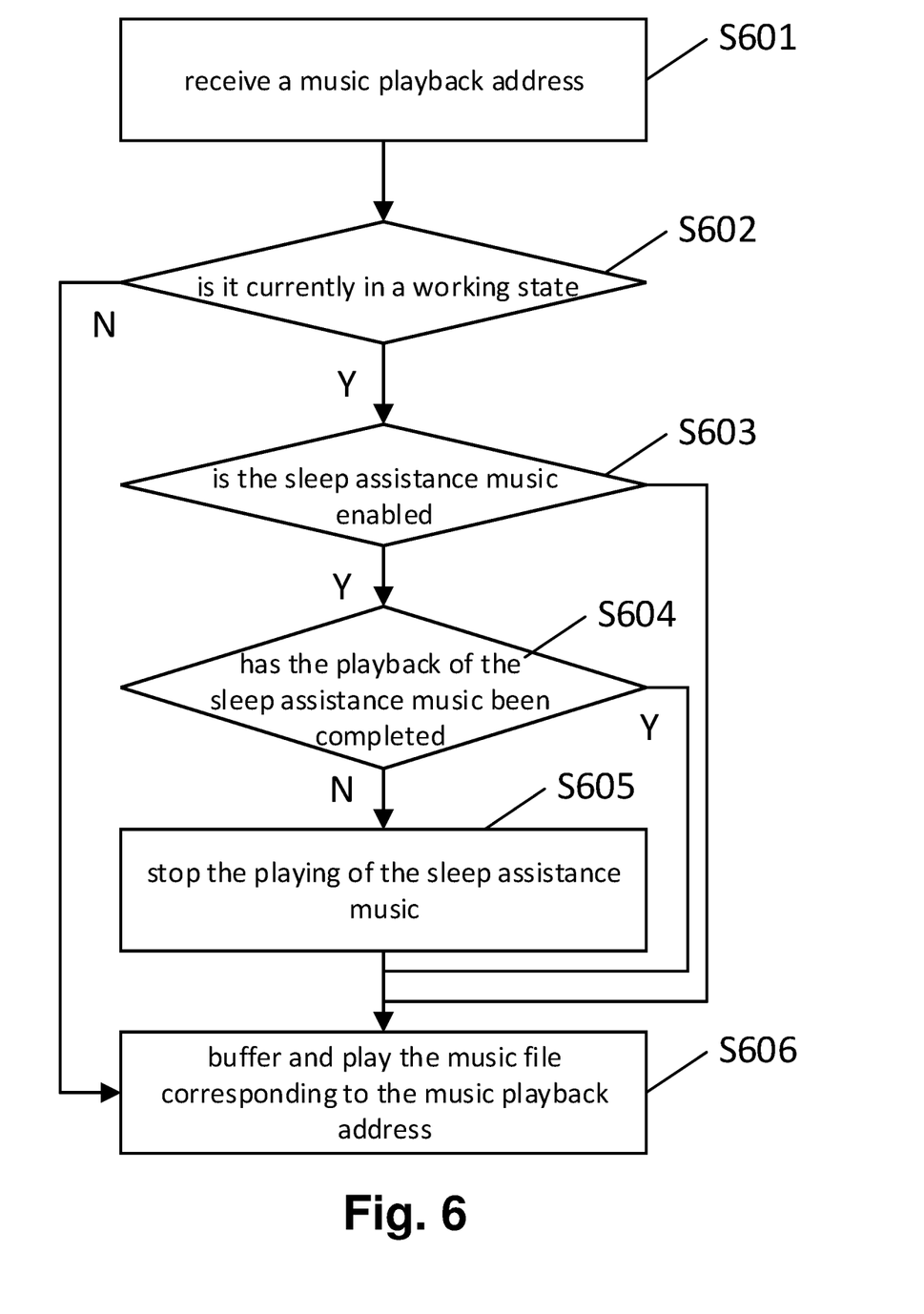
FIG. 6 is a flowchart of a method for playing music according to an embodiment of the present disclosure.

The sleep monitoring apparatus in this embodiment may also be used as a multimedia apparatus to provide users with more practical functions. FIG. 6 shows a flowchart of a method for playing music in this embodiment. When a music playback address is received, it is first determined whether the apparatus is currently in a working state (that is, monitoring mode). When in the working state, it is determined whether the sleep assistance music is enabled. If the sleep assistance music is not enabled or the playback of the sleep assistance music has been completed, the music file in the music playback address is buffered locally and played. If the sleep assistance music is enabled and the playback of the sleep assistance music has not been completed, the playing of the sleep assistance music is stopped and the music file in the music playback address is directly buffered and played. If the apparatus is currently in the standby state, the steps of buffer and playback are performed directly, and the apparatus chooses whether to enter the working state according to the user's needs after the music is played (the above steps are not shown in FIG. 6). If the apparatus does not need to enter into the working state, it can just continue to stand by after a single playback ends.

In some embodiments, because the local storage space is limited, before each time the music is buffered, it should also be checked whether the occupied space of the buffered music files exceeds the preset buffer space (the above steps are not shown in FIG. 6). If the occupied space of the buffered music files exceeds the preset buffer space, the music file with the earliest buffer time will be deleted from the buffered music files, so that the storage space is reserved for the newly buffered music file.

In this embodiment, real-time multi-dimensional monitoring of the physical sign information of the user in the sleep state is performed to improve the accuracy of the evaluation on the user's sleep quality, and to provide data support for the user to know his own sleep situation and judge his possible sleep disorder, thereby improving user experience. Some embodiments help users fall asleep through music or lights, provide users with multiple means of assisting sleep, and combine natural wake-up methods to help users cultivate healthier sleep habits.

Figure 7:
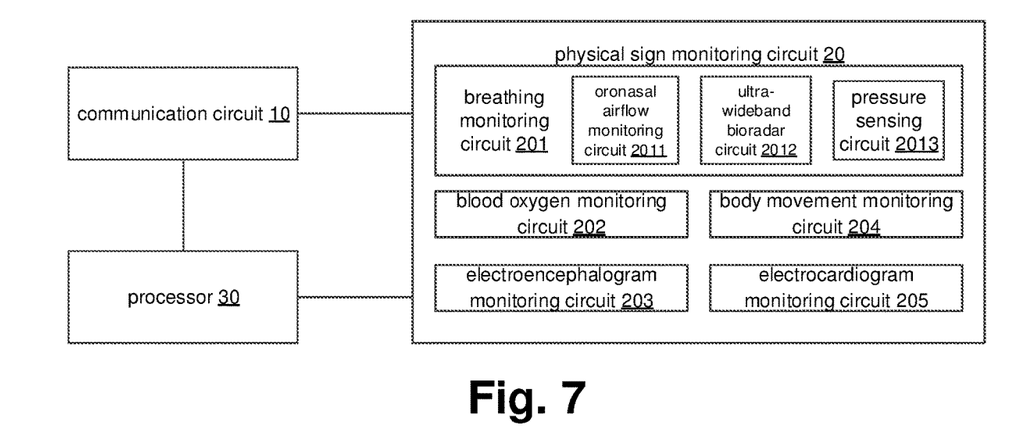
FIG. 7 is a structural diagram of a sleep monitoring device according to an embodiment of the present disclosure.

Some embodiments of the present disclosure provide a sleep monitoring device, which is mainly installed in various types of sleep monitoring apparatus with the function of monitoring the user's physical signs. The structure diagram of the device is shown in FIG. 7. The device mainly includes the following circuits coupled to each other: a communication circuit 10 configured to receive a control command from the user; a physical sign monitoring circuit 20 configured to monitor the user's physical sign information and output the physical sign information to a processor 30; the processor 30 configured to: when the communication circuit 10 receives the monitoring command, receive the physical sign information output by the physical sign monitoring circuit 20, and determine the user's sleep quality information based on the user's physical sign information. In some embodiments, the physical sign monitoring circuit may include at least one of the following monitoring circuits: a breathing monitoring circuit 201 and a blood oxygen monitoring circuit 202 configured to monitor breathing information and blood oxygen information of the user, respectively.

The communication circuit 10 mainly includes a network circuit that communicates with a network and a user's mobile terminal. The communication circuit 10 may further include a Bluetooth circuit or an infrared circuit that communicates with an external monitoring circuit. The communication circuit 10 may further include an acquisition circuit that acquires commands generated by the user by pressing, tapping, or touching on a physical button or touch area on the body of the sleep monitoring apparatus. When the sleep monitoring device is on, the communication circuit 10 receives control commands for the processor 30 to perform corresponding processing according to the control commands. Before preparing to sleep, the user usually puts the sleep monitoring device into a monitoring mode by sending a monitoring command to the sleep monitoring device. Alternatively, the user may set a time for sleep monitoring in advance, such as actively turning on the monitoring mode for sleep monitoring at 22:00 every night.

After receiving the monitoring command or reaching the preset sleep monitoring time, the physical sign monitoring circuit 20 starts to monitor the user's physical signs and obtains the corresponding physical sign information. The monitoring is performed in real time, and the physical sign monitoring circuit 20 will continuously monitor the user while the monitoring mode is on. Specifically, the current physical sign information of the user is monitored by the monitoring circuit included in the physical sign monitoring circuit 20 or other monitoring circuits that perform data communication with the sleep monitoring device through the communication circuit 10. The monitoring circuit mainly includes the breathing monitoring circuit 201 and the blood oxygen monitoring circuit 202, and in some embodiments may further include an electroencephalogram monitoring circuit 203, a body movement monitoring circuit 204, and an electrocardiogram monitoring circuit 205, which are respectively configured to monitor the electroencephalogram information, the body movement information, and the electrocardiogram information of the user. In some embodiments, the electroencephalogram monitoring circuit 203 may be for example an electroencephalogram machine, the body movement monitoring circuit 204 may be for example a motion sensor, and the electrocardiogram monitoring circuit 205 may be for example an electrocardiogram machine.

Specifically, the breathing information is information reflecting the user's breathing situation, which may be determined through information such as the oronasal airflow information, thoracoabdominal motion information, and pressure sensing information output by an oronasal airflow monitoring circuit 2011, an ultra-wideband bioradar circuit 2012, and a pressure sensing circuit 2013, respectively. The oronasal airflow monitoring circuit 2011 may be an airflow sensor placed near the user's mouth and nose, and the pressure sensing circuit 2013 may be a pressure sensor placed on the user's thoracoabdominal. The purpose is to obtain the breathing condition of the user as the monitored user's physical sign information. In addition, the determination method of the breathing information is not limited to the several methods described in this embodiment. In actual use, the breathing information of the user may also be determined through information output by other monitoring circuits, which is not limited in this embodiment.

The sleep quality information is information that reflects the user's sleep situation and is the basis for users to understand their own sleep quality. In this embodiment, the sleep quality information output by the processor 30 mainly includes the number and/or durations of sleep apnea and blood oxygen drop data, and may also include basic sleep information, such as the falling asleep time, the duration of deep sleep (that is, the deep sleep duration), the duration of light sleep (that is, the light sleep duration), and the wake-up time during this sleep. In some embodiments, the processor 30 may further generate a sleep quality report according to the sleep quality information. The above sleep quality information may be reflected in the sleep quality report in various forms such as tables, fan charts, and line charts. In addition, the sleep quality report may also provide the basis for judging the occurrence of sleep apnea and suggestions for adjustment. When the situation is relatively serious, the sleep quality report may also recommend users to seek medical treatment in a timely manner. The conclusions in the sleep quality report may be generated by the processor 30, or the physical sign information may be uploaded to a cloud server through the communication circuit 10, combined with big data for more detailed judgment.

When the user's breathing information is determined according to the oronasal airflow information, the number and/or durations of sleep apnea during the sleep process of the user may be determined by the processor 30 according to the blood oxygen information and/or the oronasal airflow information. Specifically, sleep apnea is one of the common sleep disorders. Symptoms of snoring, belching and other inability to breathe during sleep at night are common manifestations of sleep apnea. In severe cases, the cardiovascular system is involved, or asphyxia or sudden death occurs. In this embodiment, if the user develops sleep apnea, the generation of airflow will not be monitored at his or her mouth and nose. Further, in the absence of normal breathing, the user will not be supplemented with oxygen and the blood oxygen content will possibly decrease. Therefore, according to the oronasal airflow information alone or according to the blood oxygen information and the oronasal airflow information, it can be determined whether the user has sleep apnea during sleep, and the number of occurrences and/or the accumulated duration of apnea in the case of sleep apnea can be recorded and output to the user as the sleep quality information.

When the user's breathing information is determined according to the thoracoabdominal motion information, the blood oxygenation information and the thoracoabdominal motion information may be combined by the processor 30 to determine the blood oxygen drop data of the user during sleep. Specifically, the blood oxygen drop is the decrease in blood oxygen content caused by apnea. When it is severe, it may easily lead to insufficient blood supply to the heart and brain, causing serious harm to the user's body. In this embodiment, whether the user's blood oxygen has reduced is mainly determined according to the user's blood oxygen information. In some embodiments, it may be combined with the determination, through the thoracoabdominal motion information, of the breathing situation of the user to make a more accurate determination of whether the user's blood oxygen has reduced. When the user's blood oxygen has reduced, the detailed blood oxygen drop data may be recorded so that the user may subsequently know his or her condition or use the recorded data as a basis for diagnosis.

When determining the user's falling asleep time and/or awaking time, the processor 30 determines mainly by at least one of the electroencephalogram information, the electrocardiogram information and the body movement information. When the user's brain waves reflected by the electroencephalogram information are no longer excited and calm, or when the heartbeat frequency of the user is reduced according to the electroencephalogram information, or when it is reflected that the user has not experienced body movement for a period of time according to the body movement information, it can be determined that the user has entered the sleep state, otherwise it proves that the user has ended the sleep state. The corresponding time may be recorded as the user's falling asleep time or awaking time. When the thoracoabdominal motion information and/or the oronasal airflow information of the user are also obtained, the processor 30 may also determine the user's falling asleep time and awaking time based on the above physical sign information in combination with the thoracoabdominal motion information or the oronasal airflow information, in order to achieve a more accurate judgment of the user's falling asleep time and awaking time.

When determining the deep sleep duration and light sleep duration of a user, the processor 30 makes the determination mainly based on the electroencephalogram information and/or the body movement information. When using the electroencephalogram information, it is determined whether the user is in deep sleep or light sleep according to the rules reflected by the brain waves, and the duration of deep sleep and light sleep is separately counted as the sleep quality information. When using the body movement information, the processor 30 may determine the deep sleep or light sleep based on the user's body movement, but compared with the use of electroencephalogram information, the accuracy of the determination using body movement information is lower. Generally, the body movement information is used as the reference information of the electroencephalogram information. Through the combination of the electroencephalogram information and body movement information, the accuracy of the determination of deep sleep state and light sleep state is improved.

In some embodiments, in addition to monitoring the user's sleep, the embodiment can also assist the user to quickly enter the sleep state by playing sleep assistance music or lighting the breathing light, thereby helping the user to develop good sleep habits and reduce the possibility of occurrence of sleep disorders. Specifically, according to the schematic diagram of the device shown in FIG. 8, the sleep monitoring device may further include a multimedia circuit 40. When the user wishes to perform sleep assistance, the user sends a sleep assistance command to the apparatus. After the processor 30 determines that the sleep assistance command is received, it will enter the sleep assistance mode, control the multimedia circuit 40 to light at a preset frequency to help the user adjust its breathing rhythm, or control the multimedia circuit 40 to play different types of sleep assistance music to help the user relax and then quickly enter the sleep state. The user's good sleep habits may be cultivated through long-term sleep assistance. Sleep assistance music mainly includes white noise (such as water flow, raindrops, waves, and the like), sleep assistance pure music (such as soothing piano music), breathing meditation courses (such as mindfulness meditation music) or other music set by the user. The user may select which music to play for sleep assistance by sending different control commands. Therefore, in some embodiments, the multimedia circuit 40 may be for example an external audio device or a built-in audio module.

Figure 8:
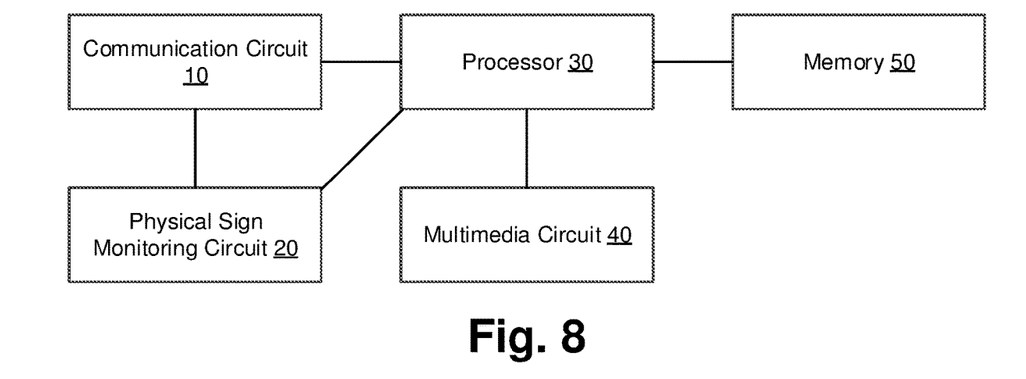
FIG. 8 is another structural diagram of a sleep monitoring device according to another embodiment of the present disclosure.

During the operation of the multimedia circuit 40, the processor 30 detects whether the user has entered the sleep state according to the monitoring command. After determining that the user has entered the sleep state, if the multimedia circuit 40 still flashes, then the brightness of the multimedia circuit 40 is gradually reduced until the multimedia circuit 40 is extinguished within a first preset duration; or if the sleep assistance music is being played, the playback volume of the sleep assistance music is gradually reduced until the sleep assistance music stops playing within a second preset duration. The first preset duration and the second preset duration may be the same or different, and the specific time is set according to user needs. Since the user is usually in a light sleep state when entering the sleep state, the user is easily awakened if there is a sudden change in brightness or ambient volume. Therefore, the effect of the external environment on the user's sleep is reduced by gradually reducing the brightness and gradually reducing the volume, thus improving the user's sleep quality. In addition, if the user has not entered the sleep state after the sleep assistance music is played or the breathing light flashes for a certain period of time, the multimedia circuit 40 is automatically turned off or waits for the user to send the sleep assistance command again.

The sleep monitoring device described in this embodiment may also provide a user with a natural wake-up function. Before going to bed, the user usually sets a wake-up device such as an alarm clock and a timer to wake up the user at a predetermined time. In this embodiment, the wake-up time set by the user is a second wake-up time, and a first wake-up time, which is earlier than the second wake-up time, is set as the time to naturally wake up the user. When the user is in the sleep state, the processor 30 continuously detects whether the current time reaches the first wake-up time, that is, whether it is the time to naturally wake up the user. If the current time reaches the first wake-up time, it is determined whether the user is in a light sleep state based on the currently acquired physical sign information of the user. During the light sleep, the user's cerebral cortex is in a relatively active stage, and it is easy to wake up the user at this time. Therefore, when the user is in the light sleep state, a wake-up device is turned on, and the prompt intensity is gradually increased to a preset intensity within a third preset duration, thus the effect of awakening the user is gradually strengthened, which prevents the user from being awakened by a sudden strong prompt and prevents user experience from being affected. If the user is not in the light sleep state at the first wake-up time, it is detected whether the current time reaches the second wake-up time set by the user, that is, the time that the user must be woken up. If the second wake-up time is reached, the wake-up device is directly turned on with the preset intensity to achieve wake-up of the user. If the second wake-up time is not reached, it is re-detected whether the first wake-up time is reached. In some embodiments, the wake-up device may be implemented by the multimedia circuit 40, for example.

Specifically, the prompting method of the wake-up device includes at least a vibration prompt and a sound prompt. When the wake-up device uses the vibration method to wake up the user, the frequency of vibration may be gradually increased within a third preset duration to continuously improve the wake-up effect on the user. When the wake-up device uses the sound prompt to wake up the user, the volume of the sound may be gradually increased within a third preset duration to continuously improve the wake-up effect on the user. The above two prompt methods may be used simultaneously, and other wake-up methods may also be added. As long as the wake-up effect for the user can be achieved, this embodiment is not limited thereto.

By awakening the user naturally in advance, this embodiment can make the user wake up more comfortable, cultivate the user's good working and rest habits, adjust the user's biological clock, and then improve the user's sleep quality and ensure a better mental state during the day. In some embodiments, the first wake-up time is earlier than the second wake-up time, and the time difference between the two may be 10 minutes or may be set by the user. The third preset duration should be less than the time difference between the first wake-up time and the second wake-up time, preferably 60 seconds, and may also be set according to user needs, which is not limited in this embodiment.

When the user needs to turn off the wake-up device, he or she may stop it by sending different stop commands. When the wake-up device is on, the processor 30 first detects whether a wake-up device stop command from the user is received. This command may be sent by a mobile terminal or generated by the user's tap or press on a key or touch area of the apparatus. For example, a long press of the touch area for three seconds corresponds to the wake-up device stop command. When the processor 30 determines that the wake-up device stop command is received, the wake-up device will be directly turned off. If the wake-up device stop command is not received, it is determined whether a wake-up device pause command is received. The wake-up device pause command may also be sent by a terminal, or generated by touching or pressing the key or touch area of the apparatus, but the way of pressing or touching should be different from that of the wake-up device stop command. For example, it may be generated by touching the touch area once. When the wake-up device pause command is received, the wake-up device is turned off temporarily to enter a nap mode, and is turned on again after a preset pause duration to receive the commands from the user again. If neither the wake-up device stop command nor the wake-up device pause command is received, the wake-up device is turned on for a fourth preset duration and then temporarily turned off, and then turned on again after a preset pause duration. If the processor 30 determines that the wake-up device stop command is never received, the wake-up device will be completely turned off after repeatedly turning on and off for a preset number of times, to prevent the user from being disturbed by the wake-up device being turned on for a long time. Specifically, each of the preset pause duration, the fourth preset duration, and the preset number of times may be set according to user needs, which is not limited in this embodiment.

When the wake-up device is turned off, the processor 30 may directly turn off the monitoring mode, and control the physical sign monitoring circuit 20 to stop monitoring the user's physical sign information. In addition, the processor 30 may turn off the monitoring mode according to the stop monitoring command. Specifically, the processor 30 detects whether the stop monitoring command sent by the user is received, and the stop monitoring command may be sent by a mobile terminal or generated by the user's tapping or pressing of the key or touch area of the apparatus. For example, a long press of a physical button for 3 seconds corresponds to the stop monitoring command. Upon receiving the stop monitoring command, the processor 30 controls the physical sign monitoring circuit 20 to stop the monitoring of the user's physical sign information in the sleep state. If the stop monitoring command is not received, it is detected whether the time difference between the user's falling asleep time and the current time reaches a fifth preset duration. The fifth preset duration may be set to the duration of a normal person's sleep, such as 8 hours. After the time difference exceeds 8 hours, the user's sleep state ends, and the monitoring of the user's physical sign information in the sleep state is automatically stopped. If it is detected that the time difference between the user's falling asleep time and the current time does not reach the fifth preset duration, the monitoring is continued until a stop monitoring command is received or the time difference reaches the fifth preset duration.

After the sleep monitoring device is turned on, the processor 30 first detects whether it is connected to the network. When not connected to the network, the processor 30 reminds the user to configure the network by flashing an indicator light or issuing an alarm sound. At this time, the user may turn on the apparatus's network configuration mode by long pressing a physical button for 5 seconds. In the network configuration mode, the apparatus continuously detects whether a network configuration command is received. The network configuration command is sent by the user's mobile terminal, and the command carries the name and password of the network. The processor 30 controls the communication circuit 10 to access the corresponding network according to the name and password of the network, so as to obtain update services or data support from the network.

The sleep monitoring device in this embodiment may also be used as a multimedia device to provide users with more practical functions. When the processor 30 determines that a music playback address is received, it is first determined whether the apparatus is currently in a working state (that is, monitoring mode). When in the working state, it is determined whether the sleep assistance music is enabled. If the sleep assistance music is not enabled or the playback of the sleep assistance music has been completed, the music file in the music playback address is buffered to the memory 50 and played through the multimedia circuit 40. If the sleep assistance music is enabled and the playback of the sleep assistance music has not been completed, the playing of the sleep assistance music is stopped and the music file in the music playback address is directly buffered and played. If the apparatus is currently in the standby state, the buffer and playback are performed directly, and the device chooses whether to enter the working state according to the user's needs after the music is played. If the device does not need to enter the working state, it may just continue to stand by after a single playback ends.

In some embodiments, because the local storage space is limited, before each time the music is buffered, the processor 30 should also check whether the occupied space of the buffered music files exceeds the preset buffer space. If the occupied space of the buffered music files exceeds the preset buffer space, the music file with the earliest buffer time will be deleted from the buffered music files, so that the storage space is reserved for the newly buffered music file.

In this embodiment, real-time multi-dimensional monitoring of the physical sign information of the user in the sleep state is performed to improve the accuracy of the evaluation on the user's sleep quality, and to provide data support for the user to know his own sleep situation and judge his possible sleep disorder, thereby improving user experience. Moreover, the sleep monitoring device in this embodiment may be integrated into a portable apparatus. Also, there is no need to connect a large number of monitoring lines on the user's body like a PSG apparatus, and the apparatus may be placed on the bedside for sleep monitoring. This reduces the manufacturing cost of the apparatus and facilitates its use by the user. Some embodiments help users fall asleep through music or lights, provide users with multiple means of assisting sleep, and combine natural wake-up methods to help users cultivate healthier sleep habits.

Figure 9:
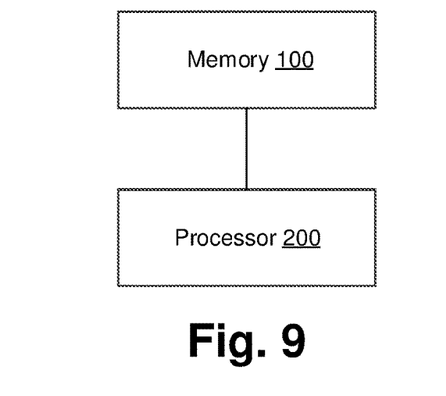
FIG. 9 is a structural diagram of a sleep monitoring apparatus according to an embodiment of the present disclosure.

A yet other embodiment of the present disclosure provides a sleep monitoring apparatus, the structure diagram of which is shown in FIG. 9. The sleep monitoring apparatus includes at least a memory 100 and a processor 200. In some embodiments, the processor 200 may comprise but not limited to one of central processing unit (CPU), graphic processing unit (GPU), digital signal processor (DSP), micro controller unit (MCU), application specific integrated circuit (ASIC), field programmable gate array (FPGA), or any other hardware for processing data. A computer program is stored on the memory 100. When the processor 200 executes the computer program on the memory 100, the following steps S1 to S3 are implemented:

S1. monitoring physical sign information of a user when receiving a monitoring command;

S2, determining the sleep quality information of the user according to the physical sign information of the user.

The breathing information determined by the processor 200 is determined according to at least one of the following information: oronasal airflow information, thoracoabdominal motion information, and pressure sensing information; the thoracoabdominal motion information is obtained through a biological radar wave.

The physical sign information determined by the processor 200 further includes at least one of the following: electroencephalogram information, body movement information, and electrocardiogram information.

The sleep quality information determined by the processor 200 includes at least: number of sleep apnea, durations of sleep apnea, and blood oxygen drop data.

The sleep quality information determined by the processor 200 further includes at least one of the following: falling asleep time, awaking time, light sleep duration, and deep sleep duration.

When the processor 200 executes the step of determining the user's sleep quality information based on the user's physical sign information on the memory 100, the processor 200 specifically executes the following computer program: in a case where the breathing information is determined according to the oronasal airflow information, determining the number and/or duration of the sleep apnea according to the oronasal airflow information or according to the blood oxygen information and the oronasal airflow information.

When the processor 200 executes the step of determining the user's sleep quality information based on the user's physical sign information on the memory 100, the processor 200 specifically executes the following computer program: in a case where the breathing information is determined according to the thoracoabdominal motion information, determining the number and/or duration of the sleep apnea according to the thoracoabdominal motion information or according to the thoracoabdominal motion information and at least one of the body movement information and the electrocardiogram information.

When the processor 200 executes the step of determining the user's sleep quality information based on the user's physical sign information on the memory 100, the processor 200 specifically executes the following computer program: in a case where the breathing information is determined according to the thoracoabdominal motion information, determining the blood oxygen drop data according to the blood oxygen information, or determining the blood oxygen drop data according to the blood oxygen information and the thoracoabdominal motion information.

When the processor 200 executes the step of determining the user's sleep quality information based on the user's physical sign information on the memory 100, the processor 200 specifically executes the following computer program: determining the falling asleep time and/or the awaking time according to at least one of: the electroencephalogram information, the electrocardiogram information, and the body movement information.

When the processor 200 executes the step of determining the user's sleep quality information based on the user's physical sign information on the memory 100, the processor 200 specifically executes the following computer program: in a case where the breathing information is determined according to the thoracoabdominal motion information and/or the oronasal airflow information, determining the falling asleep time and/or the awaking time according to at least one of: the thoracoabdominal motion information, the oronasal airflow information, the electroencephalogram information, the electrocardiogram information and the body movement information.

When the processor 200 executes the step of determining the user's sleep quality information based on the user's physical sign information on the memory 100, the processor 200 specifically executes the following computer program: determining the user's deep sleep duration and/or light sleep duration according to the electroencephalogram information and/or the body movement information.

Before executing the step of monitoring the user's physical sign information when receiving the monitoring command, the processor 200 further executes the following computer program: detecting whether a sleep assistance command is received; when the sleep assistance command is received, lighting a breathing light at a preset frequency and/or playing sleep assistance music.

After executing the step of detecting whether the user enters the sleep state on the memory 100, the processor 200 further executes the following computer program: detecting whether the user enters a sleep state according to the physical sign information; when the user enters the sleep state, gradually reducing a brightness of the breathing light until the breathing light is extinguished within a first preset duration; and/or gradually reducing a playback volume of the sleep assistance music until the sleep assistance music stops playing within a second preset duration.

The processor 200 further executes the following computer program on the memory 100: when the user enters the sleep state, detecting whether current time reaches a first wake-up time; when the current time reaches the first wake-up time, detecting whether the user is in a light sleep state according to the physical sign information; when the user is in the light sleep state, turning on a wake-up device, and gradually increasing a prompt intensity of the wake-up device to a preset intensity within a third preset duration; when the user is not in the light sleep state, detecting whether the current time reaches a second wake-up time; when the current time reaches the second wake-up time, turning on the wake-up device at the preset intensity;

wherein the first wake-up time is earlier than the second wake-up time.

The processor 200 further executes the following computer program on the memory 100: when the wake-up device is on, detecting whether a wake-up device stop command is received; if the wake-up device stop command is received, turning off the wake-up device; if the wake-up device stop command is not received, detecting whether a wake-up device pause command is received; if the wake-up device pause command is received, temporarily turning off the wake-up device, and turning on the wake-up device again after a preset pause duration; if the wake-up device pause command is not received, temporarily turning off the wake-up device after the wake-up device is turned on for a fourth preset duration, and turning on the wake-up device again after the preset pause duration; turning off the wake-up device after the wake-up device is paused for a preset number of times.

The processor 200 further executes the following computer program on the memory 100: after the wake-up device is turned off, stopping monitoring the user's physical sign information in the sleep state.

The processor 200 further executes the following computer program on the memory 100: when the user enters the sleep state, detecting whether a stop monitoring command is received; if the stop monitoring command is received, stopping the monitoring of the user's physical sign information in the sleep state; if the stop monitoring command is not received, detecting whether a time difference between the user's falling asleep time and a current time reaches a fifth preset duration; if the time difference reaches the fifth preset duration, stopping the monitoring of the user's physical sign information in the sleep state.

Before executing the step of detecting whether the user enters the sleep state on the memory 100, the processor 200 further executes the following computer program: detecting whether a network configuration command is received; upon receiving the network configuration command, connecting to a network according to a name and password of the network in the network configuration command.

The processor 200 further executes the following computer program on the memory 100: when a music playback address is received, buffering a music file corresponding to the music playback address and playing the music file.

Before executing the step of buffering the music file corresponding to the music playback address on the memory 100, the processor 200 further executes the following computer program: detecting whether a occupied space of buffered music files exceeds a preset buffer space; when the occupied space exceeds the preset buffer space, deleting a music file with the earliest buffer time among the buffered music files.

In this embodiment, real-time multi-dimensional monitoring of the physical sign information of the user in the sleep state is performed to improve the accuracy of the evaluation on the user's sleep quality, and to provide data support for the user to know his own sleep situation and judge his possible sleep disorder, thereby improving user experience. Some embodiments help users fall asleep through music or lights, provide users with multiple means of assisting sleep, and combine natural wake-up methods to help users cultivate healthier sleep habits.

A further embodiment of the present disclosure provides a non-transitory computer-readable storage medium. A computer program is stored on the storage medium, and when the computer program is executed by a processor, the sleep monitoring method in the foregoing embodiment of the present disclosure is performed.

The above embodiments are merely exemplary embodiments of the present disclosure and are not intended to limit the present disclosure. The protection scope of the present disclosure is defined by the claims. Those skilled in the art may make various modifications or equivalent substitutions to the disclosure within the essence and protection scope of the disclosure, and such modifications or equivalent substitutions should also be deemed to fall within the protection scope of the disclosure.

We claim:

1. A method for sleep monitoring, the method comprising:
   detecting whether a sleep assistance command is received;
   lighting up a breathing light at a preset frequency in response to receiving the sleep assistance command; and
   monitoring physical sign information of a user in response to receiving a monitoring command;
   detecting whether the user enters into a sleep state according to the physical sign information;
   gradually reducing a brightness of the breathing light within a first preset duration until the breathing light is extinguished in a case where the user enters into the sleep state, and
   determining sleep quality information of the user according to the physical sign information of the user, wherein the physical sign information comprises at least breathing information,
   wherein the breathing information is determined according to at least one of:
      oronasal airflow information;
      thoracoabdominal motion information; and
      pressure sensing information;
   wherein the physical sign information further comprises at least one of:
      blood oxygen information;
      electroencephalogram information;
      body movement information; and
      electrocardiogram information;
   wherein the sleep quality information comprises at least one of:
      a number of sleep apnea;
      durations of sleep apnea; and
      blood oxygen drop data;
   and
   wherein the determining the sleep quality information of the user according to the physical sign information of the user comprises:
   determining the blood oxygen drop data according to the blood oxygen information and the thoracoabdominal motion information in a case where the breathing information is determined according to the thoracoabdominal motion information.

2. The method of claim 1, wherein the thoracoabdominal motion information is obtained by using a biological radar wave.

3. The method of claim 1, wherein the determining the sleep quality information of the user according to the physical sign information of the user comprises:

determining the number and/or the durations of the sleep apnea according to the oronasal airflow information or according to the blood oxygen information and the oronasal airflow information in a case where the breathing information is determined according to the oronasal airflow information.

4. The method of claim 1, wherein the determining the sleep quality information of the user according to the physical sign information of the user comprises:
determining the number and/or the durations of the sleep apnea according to the thoracoabdominal motion information or according to the thoracoabdominal motion information and at least one of the body movement information and the electrocardiogram information in a case where the breathing information is determined according to the thoracoabdominal motion information.

5. The method of claim 1, wherein the sleep quality information further comprises at least one of:
falling asleep time;
awaking time;
light sleep duration; and
deep sleep duration.

6. The method of claim 5, wherein the determining the sleep quality information of the user according to the physical sign information of the user comprises:
determining the falling asleep time and/or the awaking time according to at least one of the electroencephalogram information, the electrocardiogram information, and the body movement information.

7. The method of claim 5, wherein the determining the sleep quality information of the user according to the physical sign information of the user comprises:
determining the falling asleep time and/or the awaking time according to at least one of the thoracoabdominal motion information, the oronasal airflow information, the electroencephalogram information, the electrocardiogram information, and the body movement information in a case where the breathing information is determined according to the thoracoabdominal motion information and/or the oronasal airflow information.

8. The method of claim 5, wherein the determining the sleep quality information of the user according to the physical sign information of the user comprises:
determining the deep sleep duration and/or light sleep duration of the user according to the electroencephalogram information and/or the body movement information.

9. The method of claim 1, the method further comprises: after detecting whether the sleep assistance command is received, playing sleep assistance music in response to receiving the sleep assistance command.

10. The method of claim 9, further comprising:
gradually reducing a playback volume of the sleep assistance music within a second preset duration until the sleep assistance music stops playing in a case where the user enters into the sleep state.

11. The method of claim 8, further comprising:
detecting whether current time reaches a first wake-up time;
detecting whether the user is in a light sleep state according to the physical sign information when the current time reaches the first wake-up time;
turning on a wake-up device and gradually increasing a prompt intensity of the wake-up device to a preset intensity within a third preset duration when the user is in the light sleep state;
detecting whether the current time reaches a second wake-up time when the user is not in the light sleep state;
turning on the wake-up device at the preset intensity when the current time reaches the second wake-up time;
wherein the first wake-up time is earlier than the second wake-up time.

12. The method of claim 11, further comprising:
detecting whether a wake-up device stop command is received when the wake-up device is on;
turning off the wake-up device when the wake-up device stop command is received;
detecting whether a wake-up device pause command is received when the wake-up device stop command is not received;
temporarily turning off the wake-up device and turning on the wake-up device again after a preset pause duration when the wake-up device pause command is received;
temporarily turning off the wake-up device after the wake-up device is turned on for a fourth preset duration and turning on the wake-up device again after the preset pause duration if the wake-up device pause command is not received;
turning off the wake-up device after the wake-up device is paused for a preset number of times.

13. The method of claim 1, further comprising:
detecting whether an occupied space of buffered music files exceeds a preset buffer space when a music playback address is received;
deleting a music file with the earliest buffer time among the buffered music files when the occupied space of the buffered music files exceeds the preset buffer space;
buffering a music file corresponding to the music playback address and playing back the music file.

14. A device for implementing the method for sleep monitoring of claim 1, the device comprising:
a communication circuit configured to receive a control command from a user;
a physical sign monitoring circuit configured to monitor the user's physical sign information and output the physical sign information to a processor; wherein the physical sign monitoring circuit comprises at least a breathing monitoring circuit configured to monitor breathing information of the user;
the processor, communicatively coupled with the communication circuit and the physical sign monitoring circuit and configured to receive the physical sign information output by the physical sign monitoring circuit when the communication circuit receives a monitoring command, and determine the sleep quality information of the user based on the physical sign information of the user.

15. The device of claim 14, further comprising:
multimedia circuit configured to emit sound and/or light according to a command.

16. A non-transitory computer-readable storage medium having stored thereon a computer program that, when executed by a processor, causes the processor to perform the method of claim 1.

* * * * *